(12) United States Patent
Kumar et al.

(10) Patent No.: US 10,966,707 B2
(45) Date of Patent: Apr. 6, 2021

(54) SURGICAL PORT CLOSURE SYSTEM

(71) Applicant: Covidien LP, Mansfield, MA (US)

(72) Inventors: Neeraj Kumar, Noida (IN); Inderjeet Singh Bhalla, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 371 days.

(21) Appl. No.: 16/157,171

(22) Filed: Oct. 11, 2018

(65) Prior Publication Data

US 2019/0200976 A1    Jul. 4, 2019

Related U.S. Application Data

(60) Provisional application No. 62/613,430, filed on Jan. 4, 2018.

(51) Int. Cl.
    *A61B 17/04*     (2006.01)
    *A61B 17/06*     (2006.01)
    (Continued)

(52) U.S. Cl.
    CPC ...... *A61B 17/0469* (2013.01); *A61B 17/0057* (2013.01); *A61B 17/0467* (2013.01);
    (Continued)

(58) Field of Classification Search
    CPC .......... A61B 17/0469; A61B 17/06066; A61B 2017/06019; A61B 17/0625; A61B 17/0482; A61B 17/0057; A61B 17/0483; A61B 17/0493; A61B 2017/047; A61B 2017/0608; A61B 2017/06042; A61B 2017/06071; A61B 2017/00477; A61B 2017/00637; A61B 2017/00663; A61B 2090/08021; A61B 2090/0811
See application file for complete search history.

(56) References Cited

U.S. PATENT DOCUMENTS 5,306,289 A     4/1994   Kaplan et al.
5,336,239 A *   8/1994   Gimpelson ........ A61B 17/0469
                                          606/223

(Continued)

FOREIGN PATENT DOCUMENTS

WO     2013160742 A1   10/2013

OTHER PUBLICATIONS

Extended European Search Report dated Jun. 4, 2019 corresponding to counterpart Patent Application EP 19150149.3.

*Primary Examiner* — Mohamed G Gabr

(57) ABSTRACT

A wound closure device includes a shaft, a needle, and a housing. The needle includes a first leg portion coupled to a distal end of the shaft, a curved portion, and a second leg portion including a needled end portion terminating at a needle tip. The housing includes a first channel slidingly engaged with the elongated body of the shaft and a second channel slidingly engageable with the second leg portion of the needle. The second channel terminates at an opening defined within a notched section defined in a proximal portion of the housing. The needle is movable to a covered position in which the needle tip is disposed within the second channel of the housing, an advanced position in which the needle tip is disposed distal to the housing, and a retracted position in which the needle tip is disposed within the notched section of the housing.

19 Claims, 6 Drawing Sheets

(51) Int. Cl.
*A61B 17/00* (2006.01)
*A61B 90/00* (2016.01)

(52) U.S. Cl.
CPC .. *A61B 17/06066* (2013.01); *A61B 17/06109* (2013.01); *A61B 2017/00477* (2013.01); *A61B 2017/00637* (2013.01); *A61B 2017/00663* (2013.01); *A61B 2017/047* (2013.01); *A61B 2017/0608* (2013.01); *A61B 2017/06042* (2013.01); *A61B 2090/0811* (2016.02); *A61B 2090/08021* (2016.02)

(56) References Cited

U.S. PATENT DOCUMENTS

| | | | |
|---|---|---|---|
| 5,439,469 A * | 8/1995 | Heaven | A61B 17/0469 112/169 |
| 5,468,251 A * | 11/1995 | Buelna | A61B 17/0469 112/169 |
| 5,503,634 A * | 4/1996 | Christy | A61B 17/0469 112/169 |
| 5,817,110 A * | 10/1998 | Kronner | A61B 17/0469 606/148 |
| 6,551,330 B1 * | 4/2003 | Bain | A61B 17/0469 606/144 |
| 8,273,105 B2 | 9/2012 | Cohen et al. | |
| 8,828,023 B2 | 9/2014 | Neff et al. | |
| 2010/0137888 A1 | 6/2010 | Wulc et al. | |
| 2016/0345953 A1 | 12/2016 | Russell et al. | |

* cited by examiner

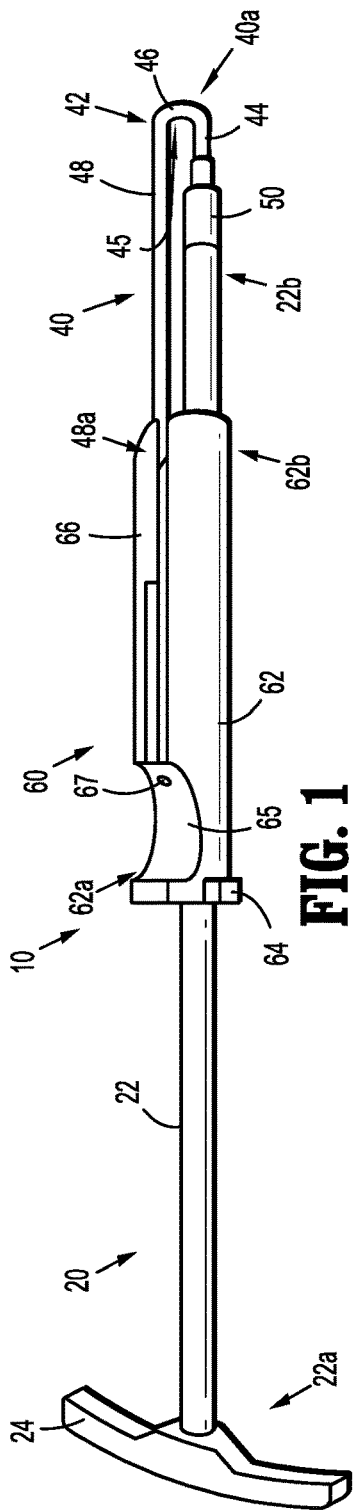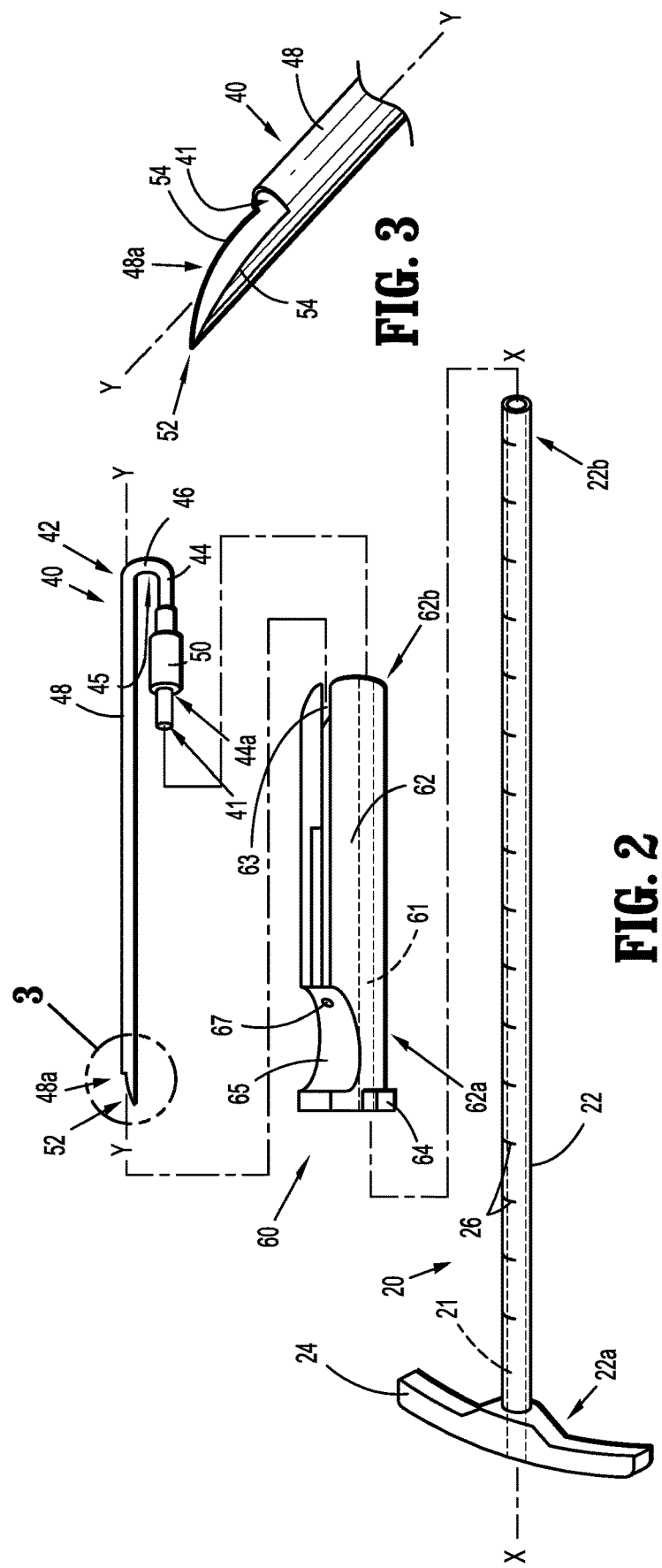

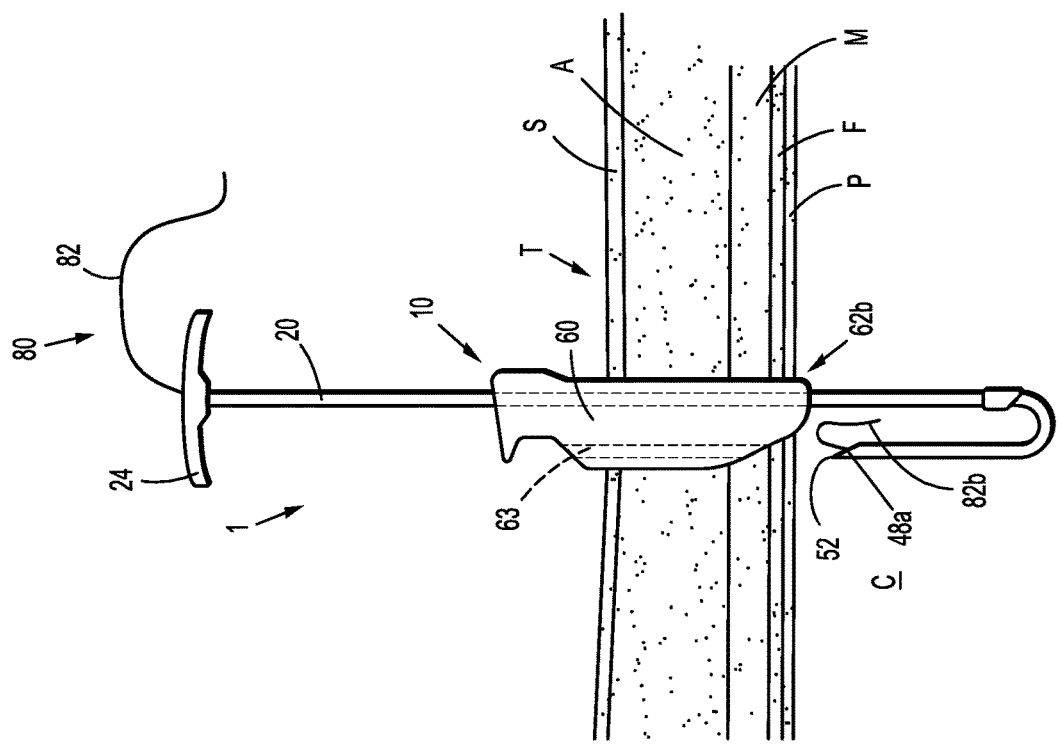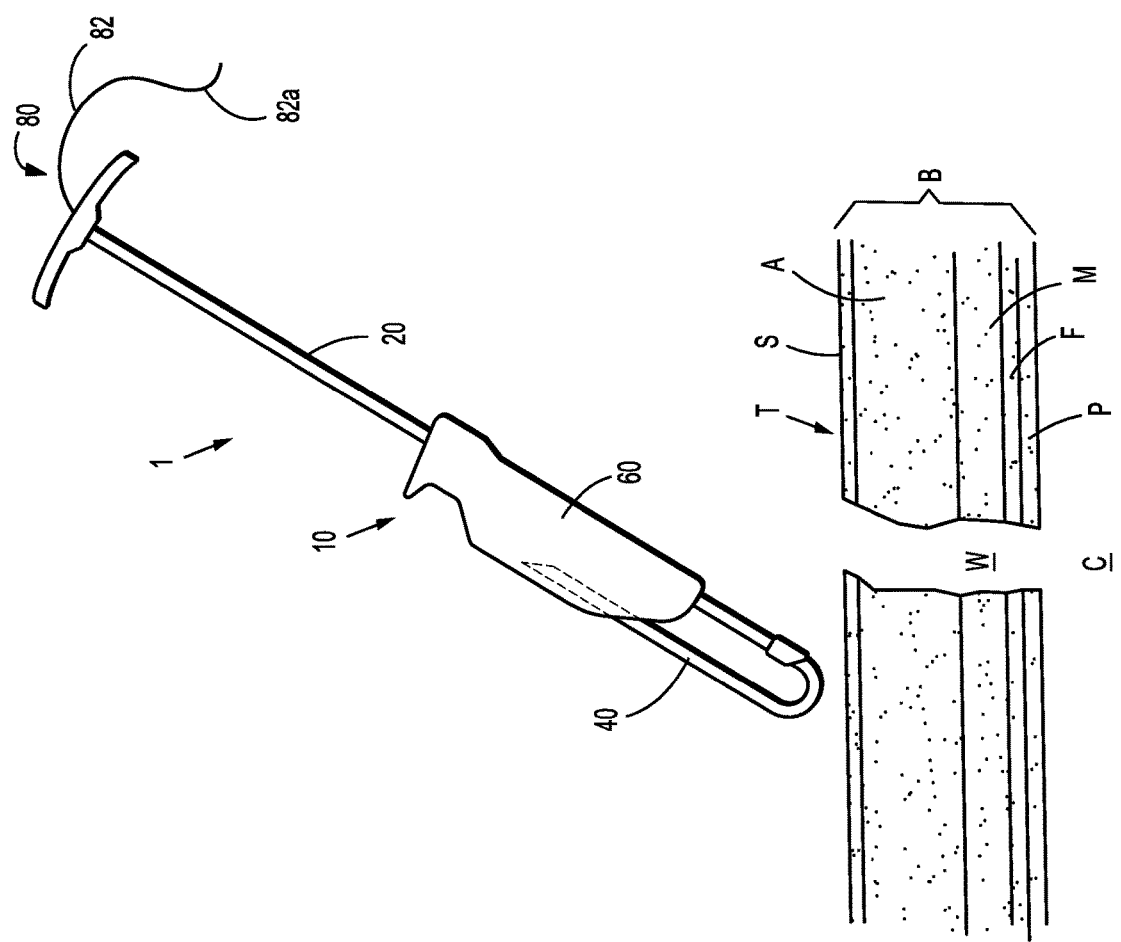

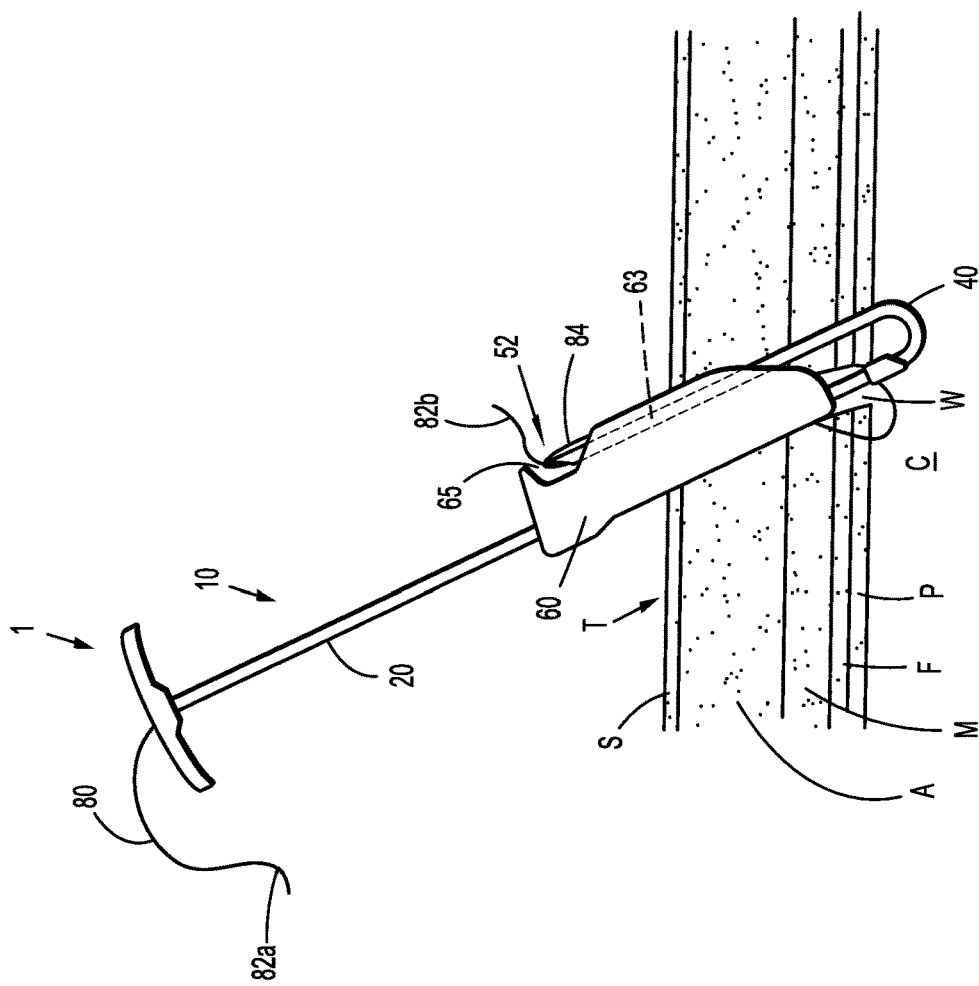
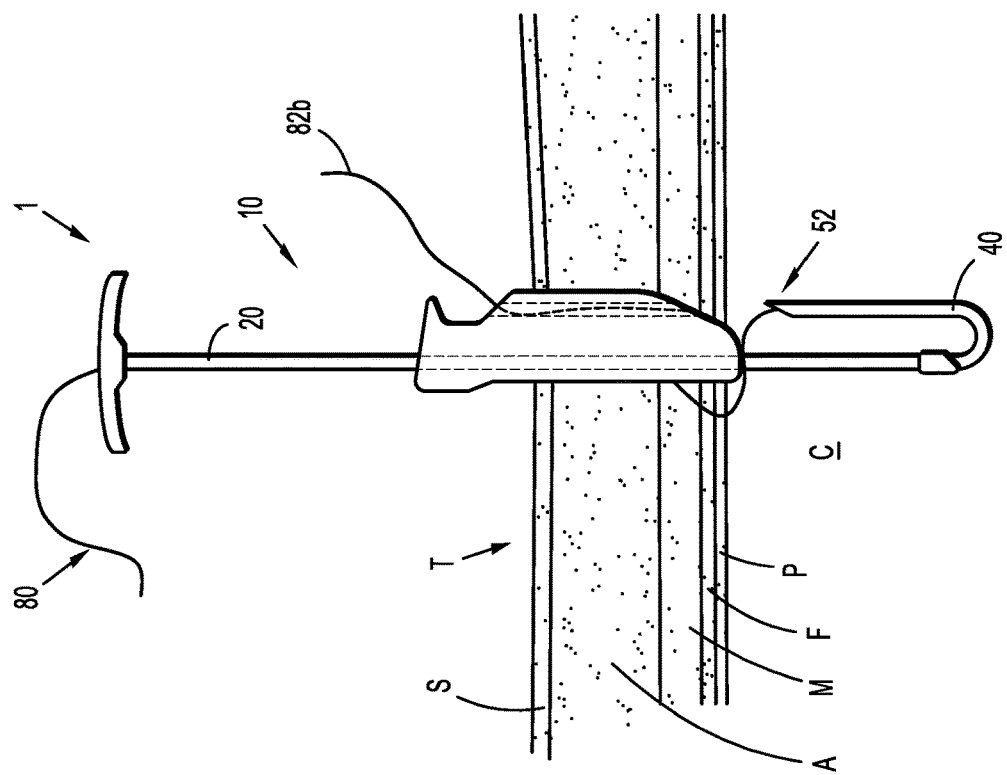

SURGICAL PORT CLOSURE SYSTEM

CROSS-REFERENCE TO RELATED APPLICATION

This application claims the benefit of and priority to U.S. Provisional Patent Application No. 62/613,430 filed Jan. 4, 2018, the entire disclosure of which is incorporated by reference herein.

TECHNICAL FIELD

The present disclosure relates to surgical devices for closing wounds and, in particular, to wound closure systems, devices, and methods for repairing perforations in tissue, such as laparoscopic port sites.

DESCRIPTION OF THE RELATED ART

Minimally invasive, e.g., endoscopic or laparoscopic, surgical procedures are operations performed within a body of a patient by using elongated surgical instruments inserted through small openings in the body. The openings may be natural passageways of the body, and/or can be incisions created by an access or tissue piercing device, such as a trocar. In laparoscopic procedures, surgery is performed in the abdomen through small incisions. Generally, laparoscopic surgical instruments are capable of being actuated outside the body while reaching remote regions within the body. The laparoscopic surgical instruments are configured to form a seal with the incision or an access port positioned within the incision through which the instruments are inserted.

Laparoscopic surgical procedures are completed by closing the incision or port site. Currently, wound closure devices, such as sutures, are used to close the port sites. Fascial closure of port sites, in particular, may be challenging and lead to intraoperative incidents such as visceral injuries due to exposure of a needle within the abdominal cavity during suturing through the fascia, increased operative time, and/or postoperative complications such as port site herniation and/or pain, especially in obese patients, due to suturing of fat and/or muscle. Accordingly, improvements in the field are desired.

SUMMARY

The present disclosure is directed to wound closure systems, devices, and methods of using same, that minimize intraoperative and postoperative complications.

According to an aspect of the present disclosure, a wound closure device includes a shaft, a needle, and a housing. The shaft includes an elongated body having a proximal end and a distal end. The needle includes a first leg portion coupled to the distal end of the shaft, a curved portion, and a second leg portion including a needled end portion terminating at a needle tip. The housing has a proximal portion including a notched section defined therein and a distal portion. The housing includes a first channel slidingly engaged with the elongated body of the shaft and a second channel slidingly engageable with the second leg portion of the needle. The second channel terminates at an opening defined within the notched section of the housing. Longitudinal movement of the shaft relative to the housing causes a corresponding longitudinal movement of the needle relative to the housing. The needle is movable to a covered position in which the needle tip is disposed within the second channel of the housing, an advanced position in which the needle tip is disposed distal to the housing, and a retracted position in which the needle tip is disposed within the notched section of the housing.

In embodiments, the shaft includes a lumen defined therethrough that is in open communication with a lumen defined through the needle. In some embodiments, the needled end portion of the needle has a substantially semi-circular configuration with the needle tip laterally offset with respect to a longitudinal axis defined through the second leg portion of the needle. In certain embodiments, the needled end portion of the needle includes arcuate edges tapering proximally towards the needle tip.

In embodiments, the second leg segment of the needle includes an opening extending therethrough that includes a first region having a smaller dimension than a second region of the opening. In some embodiments, the opening is disposed adjacent to the needled end portion of the needle, the needled end portion having a conical shape extending towards the needle tip.

The shaft may include a handle disposed at the proximal end thereof. The proximal portion of the housing may include engagement features extending laterally therefrom. A connector may connect the distal end of the shaft with the first leg portion of the needle.

In embodiments, a wound closure system includes the wound closure device and a suture coupled to the second leg portion of the needle. The suture includes a first end extending proximally of the shaft and a second end extending from the needled end portion of the needle. In some embodiments, the shaft of the wound closure device includes a lumen defined therethrough that is in open communication with a lumen defined through the needle, and the suture is positioned through the lumens of the shaft and the needle.

According to another aspect of the present disclosure, a method of closing a wound includes positioning a wound closure system into a wound, the wound closure system including a wound closure device and a suture. The wound closure device includes a shaft, a needle, and a housing. The shaft includes an elongated body having a proximal end and a distal end. The needle includes a first leg portion coupled to the distal end of the shaft, a curved portion, and a second leg portion including a needled end portion terminating at a needle tip. The housing has a proximal portion including a notched section defined therein and a distal portion. The housing includes a first channel slidingly engaged with the elongated body of the shaft and a second channel slidingly engageable with the second leg portion of the needle. The second channel terminates at an opening defined within the notched section of the housing. The suture is coupled to the second leg portion of the needle. The suture includes a first end extending outside of the wound and a second end extending from the needled end portion of the needle. The method of closing the wound further includes: moving the shaft of the wound closure device distally relative to the housing to move the needle to an advanced position in which the needle tip is disposed distal to the housing; maneuvering the wound closure device within the wound to align the needle tip with a first section of tissue to be sutured; and moving the shaft proximally relative to the housing to pass the needle tip through the first section of tissue, through the second channel of the housing, and into the notched section of the housing such that the needle is in a retracted position.

Maneuvering the wound closure device may include moving the wound closure device at an angle within the wound to align the needle tip of the needle with targeted layers of the tissue. In embodiments, the method further includes: grasping the second end of the suture from within the notched section of the housing and retaining the second end outside of the wound; and moving the shaft distally relative to the housing to move the needle to the advanced position to disengage the needle from the first section of tissue.

In embodiments, the method further includes: rotating the wound closure system within the wound; maneuvering the wound closure device to align the needle tip with a second section of tissue to be sutured; and moving the shaft proximally relative to the housing to pass the needle tip through the second section of tissue, through the second channel of the housing, and into the notched section of the housing such that the needle is in the retracted position. Rotating the wound closure system within the wound may further include rotating the wound closure system within the wound with the needle disposed in a covered position in which the needle tip is disposed within the second channel of the housing. In some embodiments, the method further includes: cutting a portion of the suture extending from the needled end portion of the needle within the notched section of the housing to form a third end of the suture and retaining the third end of the suture outside of the wound; and moving the shaft distally relative to the housing to move the needle to the advanced position to disengage the needle from the second section of tissue.

The method may include removing the wound closure device from the wound. In embodiments, the method includes moving the needle to the covered position prior to removing the wound closure device from the wound. The method may include tying the second and third ends of the suture together.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 1 is a side, perspective view of a wound closure device in accordance with an embodiment of the present disclosure;

FIG. 2 is a side, perspective view of the wound closure device of FIG. 1, with parts separated;

FIG. 3 is an enlarged, perspective view of the area of detail identified in FIG. 2;

FIG. 4 is a side, plan view of a wound closure system including the wound closure device of FIG. 1, in a covered position, and a suture, the wound closure system configured for insertion into an incision defined through an abdominal wall in accordance with an embodiment of the present disclosure;

FIG. 5 is a side, plan view of the wound closure system of FIG. 4 inserted into the incision of the abdominal wall, with the wound closure device in an advanced position;

FIG. 8 is a side, plan view of the wound closure system of FIGS. 4-7, with the wound closure device rotated for suturing of a second section of the targeted tissue layers of the abdominal wall;

FIG. 9 is a side, plan view of the wound closure system of FIGS. 4-8, with the wound closure device in the retracted position, after suturing of the second section of the targeted tissue layers of the abdominal wall;

DETAILED DESCRIPTION

Figure 7:
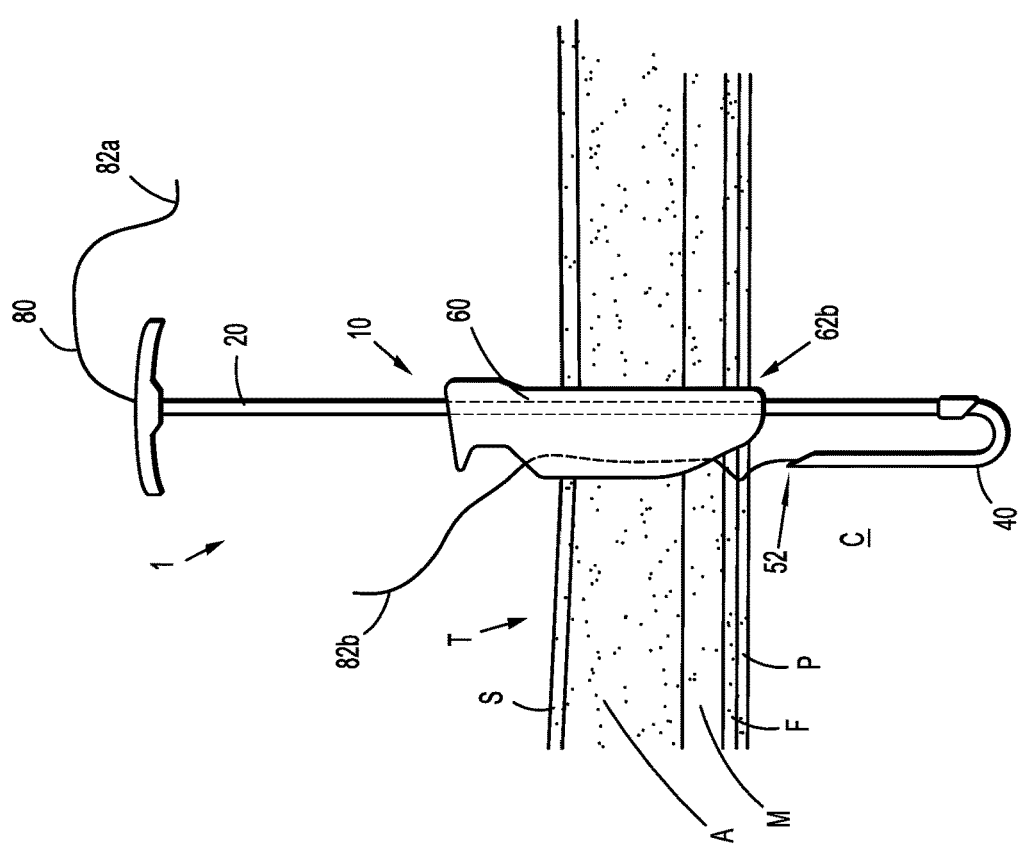
FIG. 7 is a side, plan view of the wound closure system of FIGS. 4-6, with the wound closure device in the advanced position.

Embodiments of the presently disclosed wound closure systems and devices, and method of assembling and using the same, will now be described in detail with reference to the drawing figures wherein like reference numerals identify similar or identical elements. As used herein, the term "clinician" refers to a doctor, nurse, and other clinicians or care providers, and may include support personnel. The term "patient" refers to a human subject or animal. Throughout this description, the term "proximal" refers to a portion of a system, structure, or component thereof, that is closer to a clinician, and the term "distal" refers to a portion of the structure, or component thereof, that is farther from the clinician. Directional reference terms, such as "top," "bottom," "front," "back," "side," and the like, are intended to ease description of the embodiments and are not intended to have any limiting effect on the ultimate orientations of a structure or any parts thereof.

Referring initially to FIGS. 1 and 2, a wound closure device 10 in accordance with an embodiment of the present disclosure includes a shaft 20, a needle 40 coupled to the shaft 20, and a housing 60 slidingly engaged about the shaft 20. The shaft 20 includes an elongated body 22 having a proximal end 22a and a distal end 22b, and extends along a longitudinal axis "X". While the elongated body 22 is shown having a cylindrical shape (e.g., circular in cross-sectional area), it should be understood that the elongated body 22 may have other shapes, such as oval, elliptical, etc.

A handle 24 may be disposed at the proximal end 22a of the elongated body 22. While the handle 24 is shown as a T-handle in the illustrated embodiment, the handle 24 may have other configurations suitable for use by a clinician to control movement of the shaft 20 relative to the housing 60 and/or positioning of the wound closure device 10 within tissue, as should be understood by those skilled in the art. Alternatively, the proximal end 22a of the shaft 22 may be handle free.

The shaft 20 includes a lumen 21 (FIG. 2, shown in phantom) defined therethrough that extends along the longitudinal axis "X". The lumen 21 extends through the entire length of the shaft 20 (e.g., through the elongated body 22 and the handle 24), and is configured and dimensioned to receive a suture 80 (see e.g., FIG. 4) therethrough. The shaft 20 may be available in a variety of lengths suitable for a particular surgical procedure and/or particular patient. The shaft 20 may include markings 26 disposed along the elongated body 22 to indicate, for example, the depth of insertion into tissue and/or the position of a needle tip 52 of the needle 40 relative to the housing 60 (e.g., a zone in which the needle tip 52 is shielded within the housing 60 and/or the distal spacing of the needle tip 52 relative to the housing 60).

The needle 40 includes a body 42 having a generally J-shaped configuration, and a lumen 41 defined therethrough. The lumen 41 extends through the entirety of the needle 40 and is configured and dimensioned to receive a suture 80 (see e.g., FIG. 4) therethrough. The body 42 includes a first leg portion 44, a curved portion 46 defining a distal end 40a of the needle 40, and a second leg portion 48. The first leg portion 44 includes a proximal end portion 44a including a connector 50 coupled thereto that is attachable to the distal end 22b of the elongated body 22 of the shaft 20. The connector 50 is configured to releasably or permanently secure the needle 40 to the shaft 20 such that the first leg portion 44 extends along the longitudinal axis "X" of the shaft 20, while maintaining open communication between the lumen 21 of the shaft 20 and the lumen 41 of the needle 40.

The shaft 20 and the needle 40 may be coupled together by, for example, friction fitting, press fitting, interference fitting, crimping, welding, soldering, brazing, and/or gluing the distal end 22b of the elongated body 22 of the shaft 20 between the proximal end portion 44a of the first leg portion 44 of the needle 40 and the connector 50, among other mechanical and/or chemical connection means within the purview of those skilled in the art. While the connector 50 is shown and described as being coupled to the needle 40, it should be understood that the connector 50 may be integrally formed with the needle 40 or the shaft 20, or may be a separate component attachable to the needle 40 and the shaft 20.

The curved portion 46 of the needle 40 interconnects the first and second leg portions 44, 48 and defines a substantially u-shaped recess 45 therebetween such that the curved portion 46 of the needle 40 acts as a return, reversing the direction of the body 42 of the needle 40.

The second leg portion 48 includes a proximal or needled end portion 48a terminating at a needle tip 52. As shown in FIG. 3, the needled end portion 48a of the needle 40 extends from a lateral half of the second leg portion 48 and has a substantially semi-circular, or half-cylinder, configuration including arcuate edges 54 tapering proximally towards the needle tip 52. The needle tip 52 is laterally offset with respect to a longitudinal axis "Y" defined through the second leg portion 48 of the needle 40. The needle tip 52 is pointed or sharpened for piercing tissue and, in embodiments, the arcuate edges 54 are cutting blades configured to cut through tissue. The configuration of the needled end portion 48a of the second leg portion 48 of the needle 40 allows for the retention of a suture 80 (see e.g., FIG. 5) through the lumen 41 of the needle 40 and beyond the needle tip 52 during passage of the needle 40 through the tissue. Other configurations of the needled end portion 48a and/or the needle tip 52 of the needle 40 are envisioned to effect piercing and/or cutting of tissue while retaining the suture 80 thereto.

While the needle 40 is shown as having a generally J-shaped configuration, other configurations are envisioned, for example, u-shapes, circular shapes, compound curve shapes, etc. Further, while the first and second leg portions 44, 48 of the needle 40 are shown as being substantially parallel to each other, it should be understood that the first and/or second leg portions 44, 48 may longitudinally extend at an angle with respect to the curved portion 46 so long as a needle tip 52 of the second leg portion 48 extends generally in a proximal direction and is aligned for reception within the housing 60, as discussed in detail below. The needle tip 52 of the needle 40 being oriented in a proximal direction aids in targeting tissue to be sutured as well as minimizing and/or preventing injury to surrounding tissue and/or organs.

With continued reference to FIGS. 1 and 2, the housing 60 includes a body 62 having a proximal portion 62a and a distal portion 62b. The proximal portion 62a includes a notched section 65 disposed in a lateral side of the body 62, and engagement features 64, such as protrusions or tabs, extending laterally therefrom that are configured for grasping by a clinician and/or surgical tool. Other configurations of the engagement features 64 are envisioned, such as, for example, recesses, flanges, or other structures suitable for grasping by a clinician and/or surgical tool. Alternatively, the proximal portion 62a of the housing 60 may be free of engagement features 64.

A first channel 61 (FIG. 2, shown in phantom) and a second channel 63 are defined through the body 62 of the housing 60, and are disposed in laterally spaced relation relative to each other. The first channel 61 extends the entire length of the housing 60 (e.g., through the proximal and distal portions 62a, 62b of the body 62). The first channel 61 is configured and dimensioned to receive the elongated body 22 of the shaft 20 therethrough and extends along the longitudinal axis "X" of the shaft 20. The first channel 61 has an inner dimension that is complementary to the outer dimension of the elongated body 22 such that the shaft 20 and the housing 60 are longitudinally slidable relative to each other. In embodiments, the first channel 61 of the housing 60 and the elongated body 22 of the shaft 20 are configured to allow for longitudinally slidable movement of the shaft 20 and the housing 60 relative to each other, while maintaining selective positioning of the shaft 20 relative to the housing 60 by, for example, frictional engagement of the elongated body 22 of the shaft 20 with the first channel 61 of the housing 60.

The second channel 63 extends through a portion of the body 62 of the housing 60, terminating at an opening 67 defined within the notched section 65 of the housing 60. The second channel 63 is configured and dimensioned to receive the second leg portion 48 of the needle 40 therethrough, with the notched section 65 configured and dimensioned for passage of the needled end portion 48a of the second leg portion 48 of the needle 40 therein. The second channel 63 has an inner dimension that is complementary to, or larger than, the outer dimension of the second leg portion 48 of the needle 40 such that the needle 40 is longitudinally slidable within the housing 60. The first and/or second channels 61, 63 may be fully disposed within the body 62 of the housing 60, or may be fully or partially recessed in an outer surface 66 of the housing 60.

The distal portion 62b of the housing 60 has a curved configuration tapering from a portion of the housing 60 through which the first channel 61 is disposed towards a portion of the housing 60 through which the second channel 63 is disposed. In embodiments, the distal portion 62b of the housing 60 may be curved about outer edges thereof for ease of insertion of the housing 60 into tissue.

In a method of assembling the wound closure device 10, the elongated body 22 of the shaft 20 is positioned through the first channel 61 of the housing 60 such that the proximal end 22a (e.g., the handle 24) of the elongated body 22 is disposed proximal to the proximal portion 62a of the housing 60, and the distal end 22b of the elongated body 22 is disposed distal to the distal portion 62b of the housing 60. The first leg portion 44 of the needle 40 is secured to the distal end 22b of the elongated body 22 of the shaft 20 by the connector 50, as described above. The shaft 20 is slidable relative to the housing 60 to move the needle 40 between a covered position (see e.g., FIG. 1) in which the needle tip 52 is disposed within the second channel 63 of the housing 60 and shielded therein, an advanced position (see e.g., FIG. 5), in which the needle tip 52 of the needle 40 is disposed distal to the distal portion 62b of the housing 60 and in spaced relation relative thereto to engage tissue, and a retracted position (see e.g., FIG. 6), in which the needle tip 52 is disposed within the notched section 65 of the housing 60 and accessible to a clinician. In the retracted position, the needle tip 52 of the needle 40 is disposed within the confines of the notched section 65 thereby protecting a clinician and/or surround tissue from inadvertent exposure (e.g., sticking, pricking, poking, etc.) to the needle tip 52 while providing access thereto, as described in detail below.

As shown in FIG. 4, a wound closure system 1 of the present disclosure includes the wound closure device 10 and a suture 80. The suture 80 including an elongated body 82 having a first end 82a and a second end 82b (FIG. 5). As shown in FIG. 4, in conjunction with FIG. 2, the suture 80 is threaded through the lumen 41 of the needle 40 and the lumen 21 of the shaft 20 of the wound closure device 10 such that the first end 82a of the suture 80 extends outside of the shaft 20 and the second end 82b (FIG. 5) extends outside of the needle tip 52. In embodiments, the needle 40 may be manufactured to include a suture 80 pre-threaded therethrough such that the suture 80 may be threaded through the lumen 21 of the shaft 20 prior to connecting the needle 40 to the shaft 20.

The suture 80 is fabricated from biocompatible materials which are any combination of natural, synthetic, bioabsorbable, and/or non-bioabsorbable materials. The suture 80 may be a monofilament or multifilament structure. The suture 80 may be barbless, or include barbs disposed on at least a portion thereof. In embodiments in which the suture 80 includes barbs, the barbs may be simple or compound barbs, and/or may be oriented in a unidirectional or bidirectional arrangement. For a detailed description of the structure of exemplary sutures, reference may be made to U.S. Pat. Nos. 5,306,289 and 8,273,105, the entire contents of each of which are incorporated herein by reference.

With continued reference to FIG. 4, in a method of use, the assembled wound closure system 1, with the needle 40 disposed in the covered position as shown, is inserted into an incision or wound "W" (e.g., a port site) extending through tissue "T" of an abdominal wall "B". The tissue "T" covers an abdominal cavity "C", and includes, from distal to proximal, a peritoneum "P" facing the abdominal cavity "C", fascia "F", muscle "M", fat "A", and skin "S". As shown in FIG. 5, the wound closure system 1 is positioned within the wound "W" (FIG. 4) such that the distal portion 62b of the housing 60 is disposed in the peritoneum "P" (e.g., aligned with or extends distal to) the peritoneum "P". Placement of the housing 60 of the wound closure device 10 may be determined through direct visualization as is within the purview of those skilled in the art. The shaft 20 of the wound closure device 10 is then advanced distally through the housing 60 (e.g., via handle 24) to move the needle 40 to the advanced position such that the needle tip 52 is disengaged from the second channel 63 of the housing 60 and moved into the abdominal cavity "C". The needled end 48a of the needle 40 is now freed for use.

Figure 6:
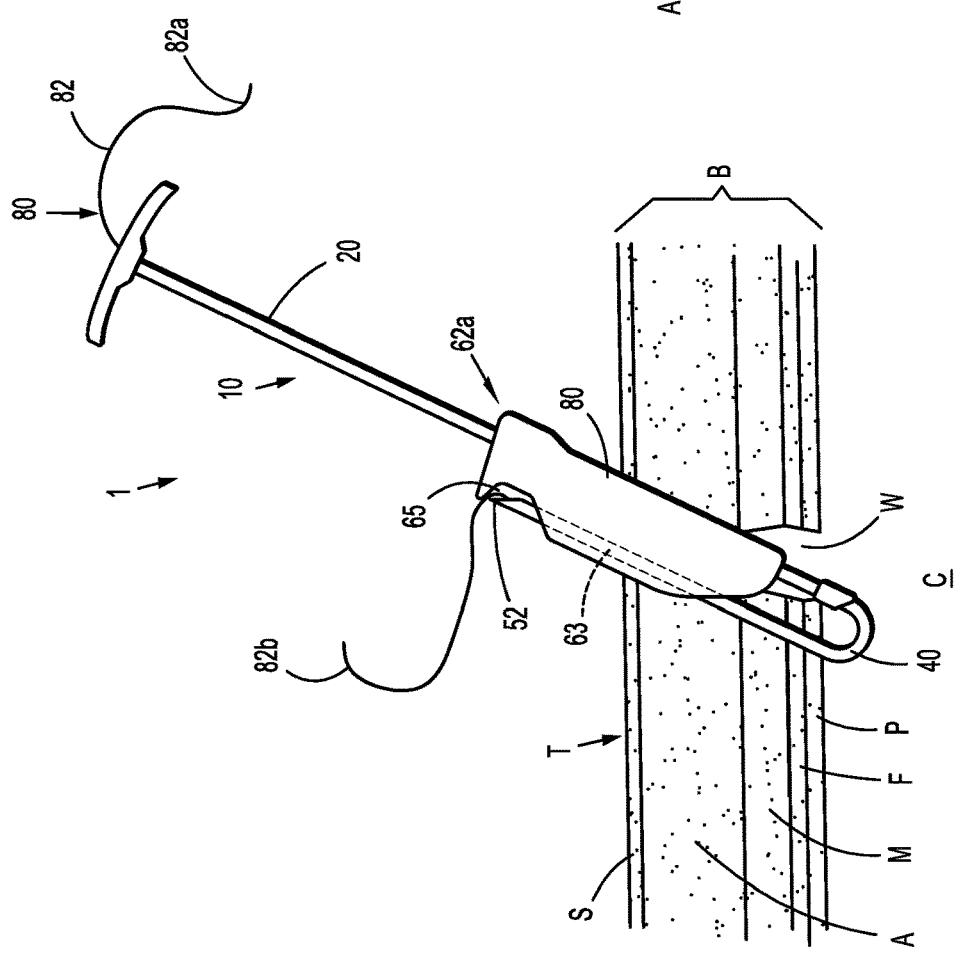
FIG. 6 is a side, plan view of the wound closure system of FIGS. 4 and 5, with the wound closure device in a retracted position, after suturing of a first section of targeted tissue layers of the abdominal wall.

As shown in FIG. 6, the wound closure system 1 is then maneuvered within the wound "W" (e.g., by changing the angle of the wound closure device 10 relative to the wound "W") to align the needle tip 52 (FIG. 5) of the needle 40 with the layers of tissue "T" to be sutured (e.g., the peritoneum "P", the fascia "F", and/or the muscle "M"), and then retracting the shaft 20 proximally to drive the needle 40 and thus, the suture 80, through the targeted layers of tissue "T" and through the second channel 63 of the housing 60 such that the needle 40 is disposed in the retracted position. In the retracted position, the needle tip 52 is positioned within the notched section 65 of the housing 60 such that a clinician can grasp the second end 82b of the suture 80 and retain the second end 82b of the suture 80 outside of the abdominal wall "B" of the patient. In some embodiments, the proximal portion 62a of the housing 60 may include a retaining member (e.g., a recess, slit, notch, etc.) to retain the second end 82b of the suture 80 outside of the tissue "T".

The configuration of the needle 40 and/or the housing 60, as well as the angle of the wound closure device 10 within the tissue "T", ensures that targeted layers of tissue "T" are captured by the needle 40 and the suture 80. As shown in the illustrated embodiments, the fascia "F" is the targeted layer of tissue "T" to be closed. Accordingly, the wound closure device 10 is angled to align the needle 40 with the peritoneum "P" and fascia "F" thereby avoiding or minimizing suturing of the muscle "M", the fat "A", and the skin "S". In some embodiments, the fascia "F" and the muscle "M" may be the targeted layers of tissue "T" for suturing.

The needle 40 is then moved back to the advanced position, as shown in FIG. 7, by moving the shaft 20 distally relative to the housing 60 such that the needle tip 52 is disengaged from the tissue "T" while retaining a portion of the suture 80 therethrough and the second end 82b of the suture 80 outside of the housing 60. The wound closure device 10 is also realigned within the wound "W" (FIG. 4) such that the distal portion 62b of the housing 60 is adjacent the peritoneum "P", as discussed above.

The wound closure device 10 is then rotated (e.g., 180°) to align the needle tip 52 of the needle 40 with the next desired section of tissue "T" to be sutured, as shown in FIG. 8. The needle 40 may be moved to the covered position (see e.g., FIG. 4) prior to rotating the wound closure device 10 to protect the tissue and/or organs disposed within the abdominal cavity "C". With the wound closure system 1 rotated and the needle 40 in the advanced position, as illustrated in FIG. 8, the wound closure system 1 is then maneuvered within the wound "W" (e.g., by manipulating the angle of the wound closure device 10 relative to the wound "W") to align the needle tip 52 of the needle 40 with the targeted layers of tissue "T" to be sutured, as shown in FIG. 9.

With continued reference to FIG. 9, the shaft 20 of the wound closure device 10 is then retracted proximally relative to the housing 60 to drive the needle 40 through the desired layers of tissue "T" (e.g., the peritoneum "P" and the fascia "F") and through the second channel 63 of the housing 60 such that the needle 40 is disposed in the retracted position. In the retracted position, the needle tip 52 of the needle 40 is positioned within the notched section 65 of the housing 60 such that a clinician can grasp and cut a portion 84 of the suture 80 extending from the needle tip 52, creating a third end 82c of the suture 80, as shown in FIG. 10.

Figure 10:
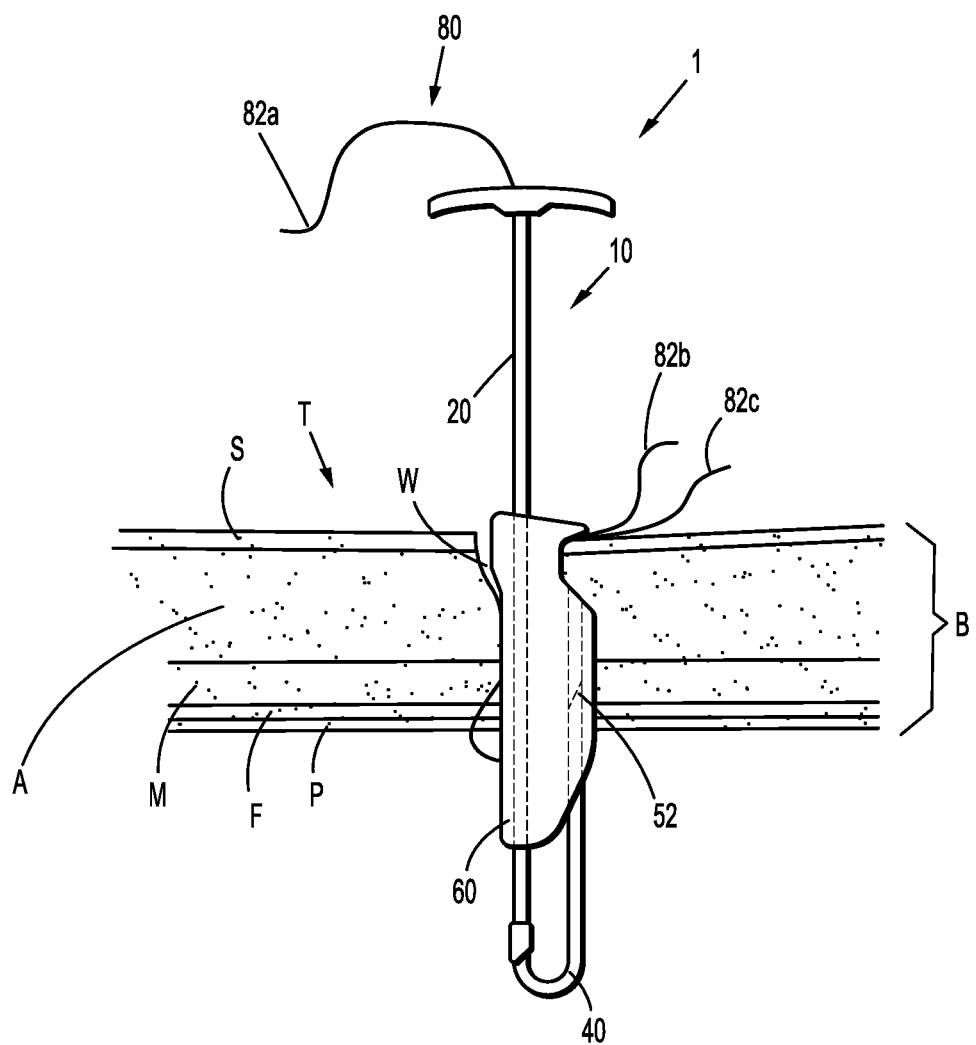
FIG. 10 is a side, plan view of the wound closure system of FIGS. 4-9, with the wound closure device in a covered position, at the end of the suturing procedure.

The needle 40 is moved back to the advanced position (see e.g., FIG. 8) such that the needle 40 is disengaged from the tissue "T" (while the third end 82c of the suture 80 is retained outside the abdominal wall "B" of the patient) and then the shaft 20 is moved proximally relative to the housing 60 to move the needle 40 to the covered position, as shown in FIG. 10. Once the needle tip 52 of the needle 40 is safely positioned within the housing 60, the wound closure system 1 is retracted from the wound "W", and the second and third ends 82b, 82c of the suture 80 are tied together to close the fascia "F".

Figure 11:
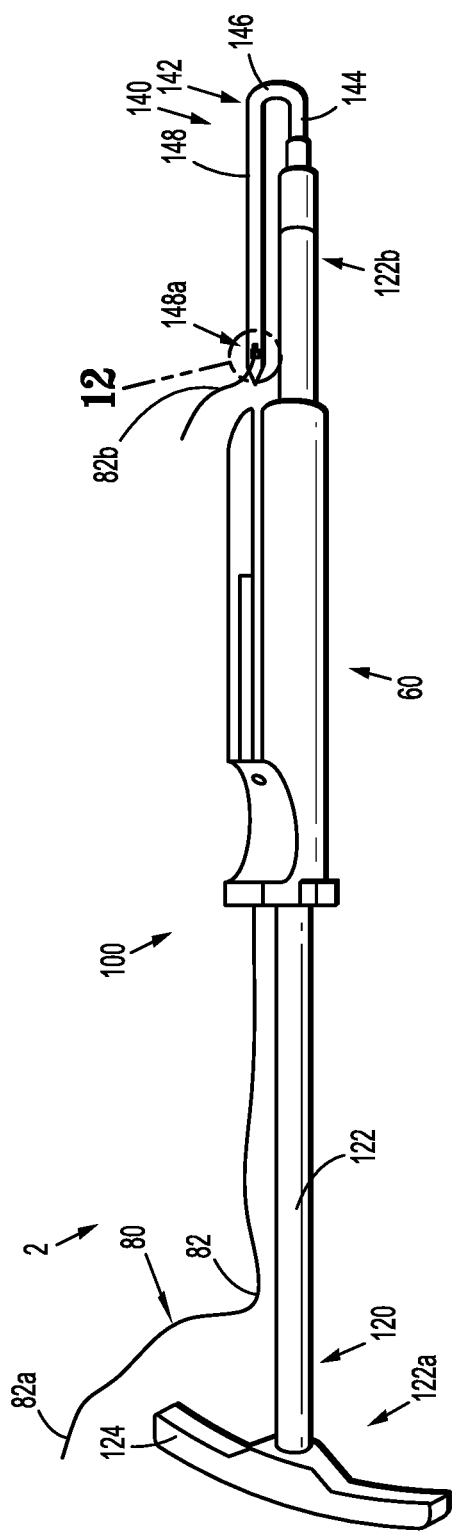
FIG. 11 is a side, perspective view of a wound closure system in accordance with another embodiment of the present disclosure.
Figure 12:
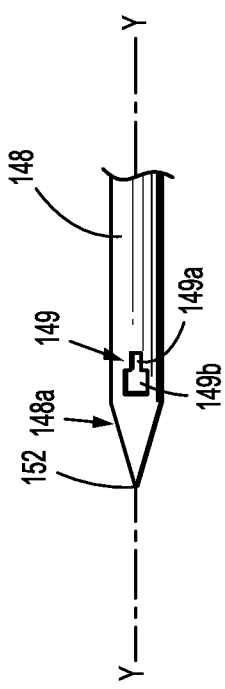
FIG. 12 is an enlarged, perspective view of the area of detail identified in FIG. 11, with a suture of the wound closure system removed.

With reference now to FIGS. 11 and 12, another embodiment of a wound closure system 2 is shown. The wound closure system 2 includes a wound closure device 100 and a suture 80. The wound closure device 100 includes a shaft 120, a needle 140, and a housing 60. The wound closure device 100 is substantially similar to the wound closure device 10 described above and will be described in detail herein to the extent necessary to describe the differences in construction and operation thereof.

The shaft 120 of the wound closure device 100 an elongated body 122 having a proximal end 122a including a handle 124 disposed thereat, and a distal end 122b. The elongated body 122 has a solid construction (e.g., does not define a lumen therethrough). Alternatively, the wound closure system 2 may include the shaft 20 of the wound closure device 10, and the lumen 21 of the shaft 20 would not be utilized during use of the wound closure system 2.

The needle 140 includes a body 142 having a generally J-shaped configuration, and including a first leg portion 144, a curved portion 146, and a second leg portion 148. A proximal or needled end portion 148a of the second leg portion 148 is conical in shape and tapers towards a pointed needle tip 152 aligned with a longitudinal axis "Y" defined through the second leg portion 148 of the needle 140. The body 142 of the needle 140 has a solid construction (e.g., does not define a lumen therethrough), except for an opening 149 extending transversely through the second leg portion 148 of the needle 140 adjacent the needled end portion 148a. It is envisioned, however, that the opening 149 may extending through the needled end portion 148a of the needle 140.

The opening 149 includes a first or proximal region 149a and a second or distal region 149b, with the distal region 149b having a larger dimension than the proximal region 149a. While the proximal and distal regions 149a, 149b of the opening 149 are each illustrated as having a substantially rectangular configuration, the proximal and distal regions 149a, 149b may have other configurations, such as substantially circular configurations forming, for example, an opening 149 having a generally figure-eight shape.

The opening 149 may be aligned with the longitudinal axis "Y" defined through the second leg portion 148 of the needle 140. The distal region 149b of the opening 149 is configured for passage of the suture 80 therethrough, and the proximal region 149a of the opening 149 is configured to retain the suture 80 therein. The suture 80 is thus passed through the distal region 149b of the opening 149 of the needle 140 and then pulled proximally such that a portion of the suture 80 is retained within the proximal region 149a of the opening 149 during use of the wound closure system 2.

The wound closure system 2 is used substantially similarly to the wound closure system 1 described above, except that the elongated body 82 of the suture 80 is disposed adjacent to the wound closure device 100, with the first end 82a of the elongated body 82 extending beyond or adjacent to the proximal end 122a of the shaft 120 and the second end 82b of the elongated body 82 extending beyond or adjacent to the opening 149 of the needle 140.

While the embodiments described above are directed to closing of port site incisions, it should be understood that the wound closure device of the present disclosure may be utilized to close other incisions and/or wounds, such as punctures, perforations, tears, rips, cuts, and other openings within a tissue having a variety of shapes (e.g., circular, non-circular, elongated, and/or non-uniform shapes) and sizes. It is envisioned that the wound closure systems of the present disclosure may be utilized to suture more than two sections of tissue together depending upon, for example, the size and/or shape of the wound. Accordingly, additional tissue sections may be sutured and a corresponding number of suture ends may be formed for tying and closing of the incision and/or wound, as should be understood by those skilled in the art.

The wound closure systems and devices of the present disclosure may be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to an operating theater or located in a remote location. In this instance, one team of surgeons or nurses may prep the patient for surgery and configure the robotic surgical system with one or more of the instruments (e.g., wound closure systems and/or devices) disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Reference is made herein to U.S. Pat. No. 8,828,023 entitled "Medical Workstation," the entire content of which is incorporated herein by reference, for a more detailed discussion of the construction and operation of an exemplary robotic surgical system.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. It is to be understood, therefore, that the present disclosure is not limited to the precise embodiments described, and that various modifications and variations of the wound closure systems, devices, and components thereof, as well as methods of assembling and using the same, will be apparent to those skilled in the art from the foregoing detailed description without departing from the scope or spirit of the present disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A wound closure device comprising:
   a shaft including an elongated body having a proximal end and a distal end;
   a needle including a first leg portion coupled to the distal end of the shaft, a curved portion, and a second leg portion including a needled end portion terminating at a needle tip; and
   a housing having a proximal portion and a distal portion, the proximal portion including a notched section defined into a side surface of the housing at a location distal of a proximal-most surface of the housing, the housing including a first channel slidingly engaged with the elongated body of the shaft and a second channel slidingly engageable with the second leg portion of the needle, the second channel terminating at an opening defined within the notched section of the housing,
   wherein longitudinal movement of the shaft relative to the housing causes a corresponding longitudinal movement of the needle relative to the housing, the needle movable to a covered position in which the needle tip is disposed within the second channel of the housing, an advanced position in which the needle tip is disposed distal to the housing, and a retracted position in which the needle tip is disposed within the notched section of the housing.

2. The wound closure device according to claim 1, wherein the shaft includes a lumen defined therethrough that is in open communication with a lumen defined through the needle.

3. The wound closure device according to claim 2, wherein the needled end portion of the needle has a substantially semi-circular configuration with the needle tip laterally offset with respect to a longitudinal axis defined through the second leg portion of the needle.

4. The wound closure device according to claim 3, wherein the needled end portion of the needle includes arcuate edges tapering proximally towards the needle tip.

5. The wound closure device according to claim 1, wherein the second leg segment of the needle includes an opening extending therethrough, the opening including a first region having a smaller dimension than a second region of the opening.

6. The wound closure device according to claim 5, wherein the opening is disposed adjacent to the needled end portion of the needle, the needled end portion having a conical shape extending towards the needle tip.

7. The wound closure device according to claim 1, wherein the shaft includes a handle disposed at the proximal end thereof.

8. The wound closure device according to claim 1, wherein the proximal portion of the housing includes engagement features extending laterally therefrom.

9. The wound closure device according to claim 1, wherein a connector connects the distal end of the shaft with the first leg portion of the needle.

10. A wound closure system comprising:
    a wound closure device according to claim 1; and
    a suture coupled to the second leg portion of the needle, the suture including a first end extending proximally of the shaft and a second end extending from the needled end portion of the needle.

11. The wound closure system of claim 10, wherein the shaft of the wound closure device includes a lumen defined therethrough that is in open communication with a lumen defined through the needle, and the suture is positioned through the lumens of the shaft and the needle.

12. A wound closure device comprising:
    a shaft including an elongated body having a proximal end and a distal end;
    a needle including a first leg portion coupled to the distal end of the shaft, a second leg portion including a needled end portion terminating at a needle tip, and a curved portion interconnecting a distal end of the first leg portion and a distal end of the second leg portion, wherein the first leg portion and the second leg portion extend parallel to one another; and
    a housing having a proximal portion and a distal portion, the proximal portion including a notched section defined into a side surface of the housing at a location distal of a proximal-most surface of the housing, the housing including a first channel slidingly engaged with the elongated body of the shaft and a second channel slidingly engageable with the second leg portion of the needle, the second channel terminating at an opening defined within the notched section of the housing,
    wherein longitudinal movement of the shaft relative to the housing causes a corresponding longitudinal movement of the needle relative to the housing, the needle movable to a covered position in which the needle tip is disposed within the second channel of the housing, an advanced position in which the needle tip is disposed distal to the housing, and a retracted position in which the needle tip is disposed within the notched section of the housing.

13. The wound closure device according to claim 12, wherein the shaft includes a lumen defined therethrough that is in open communication with a lumen defined through the needle.

14. The wound closure device according to claim 13, wherein the needled end portion of the needle has a substantially semi-circular configuration with the needle tip laterally offset with respect to a longitudinal axis defined through the second leg portion of the needle.

15. The wound closure device according to claim 14, wherein the needled end portion of the needle includes arcuate edges tapering proximally towards the needle tip.

16. The wound closure device according to claim 12, wherein the second leg segment of the needle includes an opening extending therethrough, the opening including a first region having a smaller dimension than a second region of the opening.

17. The wound closure device according to claim 16, wherein the opening is disposed adjacent to the needled end portion of the needle, the needled end portion having a conical shape extending towards the needle tip.

18. A wound closure system comprising:
a shaft including an elongated body having a proximal end and a distal end;
a needle including a first leg portion coupled to the distal end of the shaft, a second leg portion including a needled end portion terminating at a needle tip, and a curved portion interconnecting a distal end of the first leg portion and a distal end of the second leg portion;
a housing having a proximal portion and a distal portion, the distal portion including a notched section defined into a side surface of the housing at a location distal of a proximal-most surface of the housing, the housing including a first channel slidingly engaged with the elongated body of the shaft and a second channel slidingly engageable with the second leg portion of the needle, the second channel terminating at an opening defined within the notched section of the housing; and
a suture coupled to the second leg portion of the needle, the suture including a first end extending proximally of the shaft and a second end extending from the needled end portion of the needle,
wherein longitudinal movement of the shaft relative to the housing causes a corresponding longitudinal movement of the needle relative to the housing, the needle movable to a covered position in which the needle tip is disposed within the second channel of the housing, an advanced position in which the needle tip is disposed distal to the housing, and a retracted position in which the needle tip is disposed within the notched section of the housing.

19. The wound closure system of claim 18, wherein the shaft of the wound closure device includes a lumen defined therethrough that is in open communication with a lumen defined through the needle, and the suture is positioned through the lumens of the shaft and the needle.

* * * * *